United States Patent [19]

Pies et al.

[11] Patent Number: 5,436,377
[45] Date of Patent: Jul. 25, 1995

[54] PROCESS FOR ISOLATING M-DICHLOROBENZENE FROM MIXTURES OF DICHLOROBENZENE ISOMERS

[75] Inventors: Michael Pies, Duisburg; Kai Röhlk, Bergisch Gladbach; Helmut Lahr, Odenthal; Helmut Fiege, Leverkusen, all of Germany

[73] Assignee: Bayer Aktiengesellschaft, Leverkusen, Germany

[21] Appl. No.: 300,614

[22] Filed: Sep. 2, 1994

[30] Foreign Application Priority Data

Sep. 10, 1993 [DE] Germany ............ 43 30 731.0

[51] Int. Cl.⁶ ................ C07C 17/392; C07C 25/08
[52] U.S. Cl. ........................ 570/211; 570/219
[58] Field of Search .................... 570/190, 211

[56]  References Cited

U.S. PATENT DOCUMENTS

| | | | |
|---|---|---|---|
| 4,873,383 | 10/1989 | Kaneshiki et al. | 570/211 |
| 4,996,380 | 2/1991 | McCulloch et al. | 570/211 |
| 5,152,875 | 10/1992 | Rittner et al. | 570/211 |
| 5,177,302 | 1/1993 | Uemasu et al. | 585/864 |
| 5,382,725 | 1/1995 | George et al. | 570/211 |

FOREIGN PATENT DOCUMENTS

| | | |
|---|---|---|
| 0451720 | 10/1991 | European Pat. Off. |
| 2069748 | 9/1971 | France. |
| 3617137 | 11/1986 | Germany. |
| 1322020 | 7/1973 | United Kingdom. |

OTHER PUBLICATIONS

Ullmann's Encyclopedia of Industrial Chemistry, vol. A6: Ceramics to Chlorohydrins, pp. 339–340, W. Gerhartz et al., "Chlorinated Hydrocarbons".

*Primary Examiner*—Werren B. Lone
*Attorney, Agent, or Firm*—Sprung Horn Kramer & Woods

[57] ABSTRACT

In a particularly advantageous process for isolating m-dichlorobenzene from mixtures of dichlorobenzene isomers by crystallization as eutectic crystals using a processing aid, the processing aid used is a compound of the formula (I)

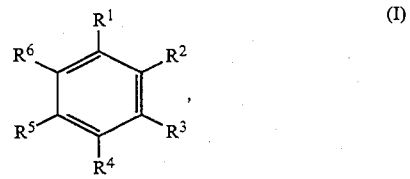

in which
$R^1$ to $R^6$ are, independently of one another, hydrogen, halogen, $C_1$–$C_4$-alkyl, hydroxyl, $NH_2$ or R—CO— having R=$C_1$–$C_4$-alkyl, with 1-bromo-4-chlorobenzene and 1,4-dibromobenzene being excepted.

11 Claims, No Drawings

PROCESS FOR ISOLATING M-DICHLOROBENZENE FROM MIXTURES OF DICHLOROBENZENE ISOMERS

The present invention relates to a particularly advantageous process for isolating m-dichlorobenzene (m-DCB) from mixtures of dichlorobenzene isomers.

m-DCB is an important intermediate, for example for the production of pharmaceuticals and pesticides.

Dichlorobenzenes are customarily prepared by chlorination of benzene or monochlorobenzene. Depending on the reaction conditions and catalysts used, mixtures of isomers having different compositions are obtained, which mixtures can contain, for example, 55-80% by weight of p-DCB, 1-3% by weight of m-DCB and 20-25% by weight of o-DCB (see Ullmanns Encyclopedia of Industrial Chemistry, 5th edition, volume A 6, page 333 ff.).

An increase in the m-DCB content in the isomer mixture is possible, for example, by means of isomerization of o- and p-DCB over catalysts, for example over aluminium trichloride or zeolites. Thus, mixtures of dichlorobenzene isomers having an m-DCB content of up to 60% by weight can be obtained.

For the separation of mixtures of dichlorobenzene isomers, in particular m-/p-DCB mixtures, into the respective pure DCB isomers, there are various processes known.

Owing to the very small boiling point differences between the individual DCB isomers (o-DCB: 180° C.; m-DCB: 173° C.; p-DCB: 174.1° C.), distillation using justifiable effort only gives a separation into o-DCB (bottom product) and an m-/p-DCB mixture (top product).

Extractive distillation processes have also already been proposed (see, for example, EP-A 451 720). These processes often require difficult-to-obtain and therefore expensive extraction agents (e.g. alkylene carbonates) without a satisfactory separation of m-DCB and p-DCB being able to be achieved.

Sulphonation or bromination of m-/p-DCB mixtures gives very selective conversion of m-DCB into sulpho- or bromo-m-DCB which can then be easily separated from unreacted p-DCB. A disadvantage here is the desulphonation or debromination which has to be subsequently carried out to obtain m-DCB again.

A combination of crystallizations and distillations (see DE-B1 2 855 940) does allow an m-DCB enrichment up to the eutectic mixture (about 85% by weight of m-DCB/about 15 % by weight of p-DCB), but the distillation is highly energy-consuming and time-consuming and is thus not particularly advantageous for industrial use.

Furthermore, it is known that p-DCB forms eutectic crystals with 1-bromo-4-chlorobenzene and with 1,4-dibromobenzene. It was therefore proposed in DE-A 3 617 137 that these substances be added to m-/p-DCB mixtures and that p-DCB be removed by crystallization in the form of eutectic crystals containing p-DCB and 1-bromo-4-chlorobenzene or 1,4-dibromobenzene. Of industrial interest are only those crystallizations which, starting from eutectic mixtures, give m-DCB in purities of over 90% by weight. With 1-bromo-4-chlorobenzene and 1,4dibromobenzene, this is only successful at temperatures in the range from −10° to −24° C. (see German Offenlegungsschrift 2 855 940, Examples 20 and 21), which requires considerable technical effort and consumption of energy.

The separation of the components of the eutectic crystals following the crystallization can be carried out by distillation. The larger the gap between the boiling points of the components in the eutectic crystals, the more rapidly and easily can they be separated from one another. The 1-bromo-4-chlorobenzene to be used according to German Offenlegungsschrift 3 617 137 boils at 196° C. It can therefore be separated from p-DCB only with considerable effort. In addition, for the isolation of pure m-DCB it is in any case advantageous in principle to crystallize the m-DCB (and not the p-DCB), since impurities in the m-/p-DCB mixture used normally remain in the mother liquor on crystallization and do not go into the crystallizate, or go into it only to a small extent.

There is therefore still a need for a process by which m-DCB can be obtained in very pure form in a simple manner.

A process has now been found for isolating m-DCB from mixtures of dichlorobenzene isomers by crystallization as eutectic crystals using a processing aid, which is characterized in that the processing aid used is a compound of the formula (I)

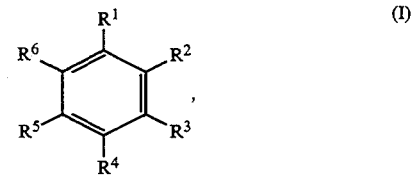

in which
$R^1$ to $R^6$ are, independently of one another, hydrogen, halogen, $C_1$-$C_4$-alkyl, hydroxyl, $NH_2$ or R—CO— having R=$C_1$-$C_4$-alkyl,
with 1-bromo-4-chlorobenzene and 1,4-dibromobenzene being excepted.

Halogen can be, for example, fluorine, chlorine or bromine; it is preferably chlorine.

Preferably, in formula (I), at least 2 of the radicals $R^1$ to $R^6$ are hydrogen and up to four of these radicals are chlorine or $C_1$- to $C_4$-alkyl, with 1,4-dibromobenzene being excepted.

Particularly preferred processing aids are tetrachlorobenzenes and cresols, in particular 1,2,3,4-tetrachlorobenzene and p-cresol.

Any mixtures of dichlorobenzene isomers are suitable for use in the process of the invention. Use is preferably made of mixtures as can be obtained after dichlorination of benzene, subsequent catalytic isomerization and distillative separation of the main amount of o-DCB. Preferred mixtures of dichlorobenzene isomers to be used can contain, for example, 80-86% by weight of m-DCB, 14-20% by weight of p-DCB and optionally up to 2% by weight of other materials.

Particular preference is given to isomer mixtures from which o-DCB has already been removed by distillation.

Processing aids of the formula (I) can be used, for example, in amounts of 20-200 parts by weight per 100 parts by weight of mixture of dichlorobenzene isomers. The amount is preferably from 50 to 130 parts by weight per 100 parts by weight of mixture of dichlorobenzene isomers.

The quality demanded of the processing aid used is not high. For example, use can be made of 1,2,3,4-tetrachlorobenzene as it is obtained by chlorination of 1,2,3-trichlorobenzene, i.e. small amounts of 1,2,3-trichlorobenzene and/or other tetrachlorobenzene isomers can also be present. 1,2,3,4-Tetrachlorobenzene having a purity of over 90% is particularly suitable.

Impurities contained in the processing aid used are generally present in the mother liquor after carrying out the process of the invention, so that after separating the components of the precipitated eutectic crystals of m-DCB and processing aid, not only the m-DCB, but also the processing and, are obtained in pure form.

The process of the invention can, for example, be carried out by first dissolving the processing aid in a mixture of dichlorobenzene isomers, optionally with slight heating, and cooling the mixture in a continuously or discontinuously operating crystallization apparatus known per se. The crystallization temperature is here generally below 20° C., preferably in the range from $-10°$ to $+10°$ C.

From the slurry present after crystallization, the liquid components (=mother liquor) can be removed in a conventional manner, for example by blowing off using a gas, filtration, decantation and/or centrifugation. After the remaining crystals have warmed up to room temperature, these can be taken from the crystallization apparatus.

From both fractions separated off (mother liquor and remelted crystals), dichlorobenzenes can be separated off from the processing aid by simple distillation and the processing aid can be reused. From the remelted crystals, m-DCB is obtained in a purity of generally above 94% by weight, and from the distillation of the mother liquor there are obtained m-/p-DCB mixtures which can again be fed to the process of the invention.

The process of the invention has a series of advantages: thus, the processing aids to be used can be obtained easily and cheaply, they have boiling points which make possible their separation from mixtures with dichlorobenzenes by a simple distillation and they make the crystallization process (crystallization of the eutectic mixtures of m-DCB and processing aid) occur at higher temperatures than hitherto. They are therefore technically simpler and more economical to carry out than known processes.

EXAMPLES

Example 1 (see also Table 1)

138 g of the mixture of various dichlorobenzenes and contaminated 1,2,3,4-tetrachlorobenzene were cooled to 5° C. in a double-walled glass cylinder (500 mm × 17 mm). After crystallization commenced, the temperature rose to up to +8° C. Within 1 hour, the precipitated crystals extended over the whole crystallization space. Subsequently, the glass cylinder was opened at the bottom and the mother liquor allowed to drain out. After the mother liquor had drained out, the cooling was turned off and at room temperature the precipitated crystals then drained out in molten form. The crystal melt thus obtained contained m-DCB in a purity of 96.5% by weight, based on dichlorobenzenes present. Further details are shown in Table 1. The % by weight therein were determined by gas chromatography.

Example 2 (see also Table 2)

10 g of the mixture of various dichlorobenzenes and p-cresol were cooled to −10° C. in a glass cylinder having a capacity of 50 ml. The crystals spontaneously formed on stirring with a glass rod were freed of mother liquor by means of filtration with suction. After turning off the cooling, 5 g of a crystal melt were obtained. The further details are shown in Table 2. The % by weight therein were determined by gas chromatography.

TABLE 1

|  | Mixture used 138 g | Mother liquor separated off 58.7 g | Crystal melt 79.3 g |
|---|---|---|---|
| m-DCB (% by weight) | 40.2 | 42.4 | 38.2 |
| p-DCB (% by weight) | 6.8 | 14.0 | 1.4 |
| Weight ratio m-/p-DCB | 85:15 | 75:25 | 96.5:3.5 |
| 1,2,3-Trichlorobenzene (% by weight) | 0.4 | 0.7 | 0.15 |
| 1,2,3,4-Tetrachlorobenzene (% by weight) | 52.3 | 42.0 | 60.2 |
| Other tetrachlorobenzenes (% by weight) | 0.37 | 0.86 | <0.2 |

TABLE 2

|  | Mixture used 10 g | Mother liquor separated off 5 g | Crystal melt 5 g |
|---|---|---|---|
| m-DCB (% by weight) | 42.5 | 45.2 | 39.6 |
| p-DCB (% by weight) | 7.5 | 12.4 | 2.6 |
| Weight ratio m-/p-DCB | 85:15 | 78.5:21.5 | 94:6 |
| p-Cresol | 50 | 41.9 | 57.8 |

What is claimed is:

1. A process for isolating m-dichlorobenzene from mixtures of dichlorobenzene isomers by crystallization as eutectic crystals using as processing aid a compound of the formula (I)

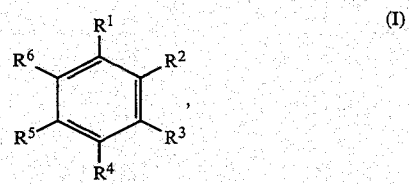

in which
R$^1$ to R$^6$ are, independently of one another, hydrogen, halogen, C$_1$-C$_4$-alkyl, hydroxyl, NH$_2$ or R—CO— having R=C$_1$-C$_4$-alkyl,
with 1-bromo-4-chlorobenzene and 1,4-dibromobenzene being excepted.

2. The process of claim 1, in which in formula (I) at least 2 of the radicals R$^1$ to R$^6$ are hydrogen and up to 4 of these radicals are chlorine or C$_1$-C$_4$-alkyl, with 1,4-dibromobenzene being excepted.

3. The process of claims 1, in which tetrachlorobenzenes are used as processing aids.

4. The process of claim 1, in which cresoles are used as processing aid.

5. The process of claim 1, in which from 20 to 200 parts by weight of the processing aid are used per 100 parts by weight of mixture of dichlorobenzene isomers.

6. The process of claims 1, in which the mixtures of dichlorobenzene isomers used are ones containing 80–86% by weight of m-DCB, 14–20% by weight of p-DCB and 0 to 2% by weight of other materials.

7. The process of claim 1, in which the crystallization temperature is below +20° C.

8. The process of claim 1, in which the crystallization temperature is in the range from −10° C. to +15° C.

9. The process of claim 1, in which after crystallization, the mother liquor is collected and the molten eutectic crystals are collected separately therefrom.

10. The process of claim 1, in which the processing aid used is separated off from the mother liquor and the molten mixture of the eutectic crystals by distillation and is recirculated to the process of the invention.

11. The process of Claim 9, in which the proportions of dichlorobenzene present in the mother liquor and the molten eutectic crystals are separated therefrom, with the mother liquor giving a m-/p-dichlorobenzene mixture which is again fed to the process of the invention and the molten eutectic crystals giving m-dichlorobenzene having a purity of above 90% by weight.

* * * * *